United States Patent
Pohlman et al.

(10) Patent No.: US 9,907,309 B2
(45) Date of Patent: Mar. 6, 2018

(54) PESTICIDAL MIXTURES

(71) Applicant: BASF SE, Ludwighsafen (DE)

(72) Inventors: Matthias Pohlman, Freinsheim (DE); Markus Gewehr, Kastellaun (DE); Egon Haden, Speyer (DE); Juergen Langewald, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/592,378

(22) Filed: Jan. 8, 2015

(65) Prior Publication Data

US 2015/0126560 A1    May 7, 2015

Related U.S. Application Data

(62) Division of application No. 13/700,180, filed as application No. PCT/EP2011/058705 on May 27, 2011, now Pat. No. 8,962,524.

(60) Provisional application No. 61/349,230, filed on May 28, 2010.

(30) Foreign Application Priority Data

May 28, 2010    (EP) .................................... 10164318

(51) Int. Cl.
| | | |
|---|---|---|
| A01N 53/00 | (2006.01) | |
| A01N 43/56 | (2006.01) | |
| A01N 43/90 | (2006.01) | |
| A01N 43/40 | (2006.01) | |

(52) U.S. Cl.
CPC ............. *A01N 43/90* (2013.01); *A01N 43/40* (2013.01); *A01N 43/56* (2013.01); *A01N 53/00* (2013.01)

(58) Field of Classification Search
CPC combination set(s) only.
See application file for complete search history.

(56) References Cited

U.S. PATENT DOCUMENTS

| | | |
|---|---|---|
| 7,491,738 B2 | 2/2009 | Goto et al. |
| 8,263,778 B2 | 9/2012 | Goto et al. |
| 2010/0035753 A1 | 2/2010 | Dietz et al. |
| 2010/0113525 A1 | 5/2010 | Horikoshi et al. |
| 2010/0281584 A1 | 11/2010 | Horikoshi et al. |

FOREIGN PATENT DOCUMENTS

| | | |
|---|---|---|
| EP | 2107060 | 10/2009 |
| EP | 2 119 361 | 11/2009 |
| EP | 2 223 599 | 9/2010 |
| KR | 2009-0108735 | 10/2009 |
| KR | 2009-0119915 | 11/2009 |
| WO | WO 2006/129714 | 12/2006 |
| WO | WO 2008/108491 | 9/2008 |
| WO | WO 2009/022702 | 2/2009 |
| WO | WO 2009/081851 | 7/2009 |
| WO | WO 2009/098223 | * 8/2009 |
| WO | WO 2011/147952 | 12/2011 |

OTHER PUBLICATIONS

Lasota, Joan A., "Avermectins, a novel class of compounds: implications for use in Arthropod pest control", Annu. Rev. Entoml. 1991, p. 91-117, vol. 36.
Office Action dated Nov. 13, 2014 in U.S. Appl. No. 13/700,182, filed Nov. 27, 2012.
Bartlett, Dave W., et al. "Review the strobilurin fungicides", Pest Management Science, 2002, p. 649-662, vol. 58.

\* cited by examiner

*Primary Examiner* — John Pak
(74) *Attorney, Agent, or Firm* — Brinks Gilson & Lione

(57) ABSTRACT

The present invention relates to a mixture comprising [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cyclopropanecarboxylate and a fungicidal compound II in synergistic effective amounts, to the use of this mixture for controlling pests and for improving the plant health and to plant propagation material comprising this mixture.

8 Claims, No Drawings

PESTICIDAL MIXTURES

This application is a divisional of U.S. application Ser. No. 13/700,180, filed Nov. 27, 2012, the entire contents of which is hereby incorporated herein by reference. U.S. application Ser. No. 13/700,180, is a National Stage application of International Application No. PCT/EP2011/058705 filed May 27, 2011, which claims the benefit of U.S. Provisional Application No. 61/349,230, filed May 28, 2010, the entire contents of which are hereby incorporated herein by reference. This application also claims priority under 35 U.S.C. § 119 to European Patent Application No. 10164318.7, filed May 28, 2010, the entire contents of which is hereby incorporated herein by reference.

The present invention relates to synergistic mixtures comprising
1) the insecticidal compound of formula I

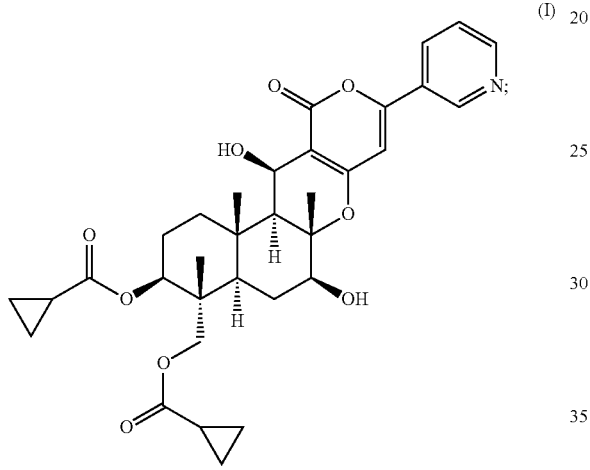

and
2) one or more, e.g. 1, 2, 3 or 4, specifically one fungicidal compound II selected from
A) the group of strobilurin fungicides consisting of azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; or from
B) the group of carboxanilides consisting of fluxapyroxad, bixafen, penflufen, penthiopyrad, isopyrazam, sedaxane, benalaxyl, benalaxyl-M, benodanil, boscalid, carboxin, fenfuram, fenhexamid, flutolanil, furametpyr, isotianil, kiralaxyl, mepronil, metalaxyl, ofurace, oxadixyl, oxycarboxin, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide; or from
C) the group of carboxylic morpholides consisting of dimethomorph, flumorph, pyrimorph; or from
Cc) the group consisting of benzimidazoles or benzimidazole releasing precursors consisting of thiophanate, thiophanate methyl, debacarb and furophanate; or from
D) the group of benzoic acid amides consisting of flumetover, fluopicolide, fluopyram, zoxamide; or from
E) the carboxamides carpropamid, dicyclomet, mandipropamid, oxytetracyclin, silthiofam and N-(6-methoxy-pyridin-3-yl)cyclopropanecarboxylic acid amide; or from
F) the group of azole fungicides, such group consisting of the triazoles fungicides azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; and of the
imidazole fungicides cyazofamid, imazalil, pefurazoate, prochloraz, triflumizol; and of the
and of the azoles ethaboxam, etridiazole, hymexazole and 2-(4-chloro-phenyl)-N-[4-(3,4-dimethoxy-phenyl)-isoxazol-5-yl]-2-prop-2-ynyloxy-acetamide; or from
G) the group of pyridines consisting of fluazinam, pyrifenox, 3-[5-(4-chloro-phenyl)-2,3-dimethyl-isoxazolidin-3-yl]pyridine, 3-[5-(4-methyl-phenyl)-2,3-dimethyl-isoxazolidin-3-yl]-pyridine; or from
H)—the group of pyrimidines consisting of bupirimate, cyprodinil, diflumetorim, fenarimol, ferimzone, mepanipyrim, nitrapyrin, nuarimol, pyrimethanil; or from
I) the group of piperazines consisting of triforine; or from
J) the group of pyrroles consisting of fenpiclonil, fludioxonil; or from
K) the group of morpholines consisting of aldimorph, dodemorph, dodemorphacetate, fenpropimorph, tridemorph; or from
L) the group of piperidines consisting of fenpropidin; or from
M) the group of dicarboximides consisting of fluoroimid, iprodione, procymidone, vinclozolin; or from
N) the group of non-aromatic 5-membered heterocycles consisting of famoxadone, fenamidone, flutianil, octhilinone, probenazole, 5-amino-2-isopropyl-3-oxo-4-orthotolyl-2,3-dihydro-pyrazole-1-carbothioic acid S-allyl ester; or from
O) the group consisting of the fungicides acibenzolar-S-methyl, ametoctradin, amisulbrom, anilazin, blasticidin-S, captafol, captan, chinomethionat, dazomet, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo[1,5-a]pyrimidine; or from
P) the thio- and dithiocarbamates ferbam, mancozeb, maneb, metam, methasulphocarb, metiram, propineb, thiram, zineb and ziram; or from
Q) the carbamates benthiavalicarb, diethofencarb, iprovalicarb, propamocarb, propamocarb hydrochlorid, valifenalate and N-(1-(1-(4-cyano-phenyl)ethanesulfonyl)-but-2-yl)carbamic acid-(4-fluorophenyl)ester; or from
R) the guanidine fungicides consisting of guanidine, dodine, dodine free base, guazatine, guazatine-acetate, iminoctadine, iminoctadine-triacetate and iminoctadine-tris(albesilate); or from S) the antibiotic fungicides consisting of kasugamycin, kasugamycin hydrochloridehydrate, streptomycin, polyoxine and validamycin A; or from
T) the nitrophenyl derivates consisting of binapacryl, dicloran, dinobuton, dinocap, nitrothal-isopropyl and tecnazen, or from
U) the organometal compounds consisting of fentin salts, such as fentin-acetate, fentin chloride or fentin hydroxide; or from
V) sulfur-containing heterocyclyl compounds consisting of dithianon, isoprothiolane; or from
W) organophosphorus compounds consisting of edifenphos, fosetyl, fosetylaluminum, iprobenfos, phosphorous acid and its salts, pyrazophos, tolclofosmethyl; or from
X) organochlorine compounds consisting of chlorothalonil, dichlofluanid, dichlorophen, flusulfamide, hexachlorobenzene, pencycuron, pentachlorphenole and its salts, phthalide, quintozene, tolylfluanid, N-(4-chloro-2-nitro-phenyl)-N-ethyl-4-methyl-benzenesulfonamide; or from
Y)—inorganic active substances consisting of Bordeaux mixture, copper acetate, copper hydroxide, copper oxychloride, basic copper sulfate, sulfur; or from
Z) antifungal biocontrol agents, plant bioactivators consisting of *Ampelomyces quisqualis, Aspergillus flavus, Aureobasidium pullulans, Bacillus pumilus, Bacillus subtilis, Bacillus subtilis* var. *amyloliquefaciens* FZB24, *Candida oleophila* I-82, *Candida saitoana, Clonostachys rosea* f. *catenulata*, also named *Gliocladium catenulatum Coniothyrium minitans, Cryphonectria parasitica, Cryptococcus albidus, Fusarium oxysporum, Metschnikowia fructicola, Microdochium dimerum, Phlebiopsis gigantea, Pseudozyma flocculosa, Pythium oligandrum* DV74, *Reynoutria sachlinensis, Talaromyces flavus* V117b, *Trichoderma asperellum* SKT-1, *T. atroviride* LC52, *T. harzianum* T-22, *T. harzianum* TH 35, *T. harzianum* T-39, *T. harzianum* and *T. viride, T. harzianum* ICC012 and *T. viride* ICC080, *T. polysporum* and *T. harzianum, T. stromaticum, T. virens* GL-21, *T. viride, T. viride* TV1, *Uloclanium oudemansii* HRU3; or from
Ab) the group consisting of the fungicides biphenyl, bronopol, cyflufenamid, cymoxanil, diphenylamin, metrafenone, pyriofenone, mildiomycin, oxin-copper, prohexadione-calcium, spiroxamine, tebufloquin, tolylfluanid, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide;
in synergistic effective amounts.

Hereinbelow, the compound of formula I is named "compound I".

The mixture according to the invention may be a physical mixture of the compound I and the at least one compound II. Accordingly, the invention also provides a physical mixture comprising the compound I and at least one compound II. However, the mixture may also be any combination of the compound I with at least one compound II, it not being required for compounds I and II to be present together in the same formulation.

An example of a mixture according to the invention in which compound I and the at least one compound II are not present together in the same formulation is a kit of parts. In a kit of parts, two or more components of a kit are packaged separately, i.e., not preformulated. Further details are explained below.

The present invention further relates to binary mixtures comprising the compound of formula I and one compound of formula II.

The present invention also relates to ternary mixtures comprising the compound of formula I and two different compounds of formula II or the compound of formula I, one compound of formula II and one further active compound III, where compound III is selected from insecticides different from compound I and fungicides different from compounds II and preferably from insecticides different from compound I, in synergistically effective amounts.

Preferably, the present invention relates to ternary mixtures comprising the compound of formula I and two different compounds II, wherein compounds II are selected from thiophanate-methyl, metalaxyl, azoxystrobin, pyraclostrobin, trifloxystrobin, prochloraz, fludioxonil, dimethomorph, triticonazole, difenoconazole, kresoxim-methyl, boscalid, fluopyram, fluxapyroxad, penflufen, penthiopyrad, sedaxane and pyrimethanil in synergistically effective amounts.

Alternatively preferably, the present invention relates to ternary mixtures comprising the compound of formula I, one compound II and one compound III, wherein
a) compound II is selected from azoxystrobin, pyraclostrobin, trifloxystrobin, kresoxim-methyl, fluopyram, fluxapyroxad, penflufen, penthiopyrad and sedaxane; and
b) compound III is selected from clothianidine, imidacloprid, thiamethoxam and fipronil;
in synergistically effective amounts.

The present invention also relates to quaternary mixtures comprising the compound of formula I and three different compounds of formula II, or the compound of formula I, two different compounds of formula II and one further active compound III, or, preferably, the compound of formula I, one compound of formula II and two further active compounds III, where compound III is as defined above, in synergistically effective amounts.

Preferably, the present invention also relates to quaternary mixtures comprising the compound of formula I, one compound II and two compounds III, wherein
a) compound II is selected from azoxystrobin, pyraclostrobin, trifloxystrobin, kresoxim-methyl, fluopyram, fluxapyroxad, penflufen, penthiopyrad and sedaxane; and
b) compound III (1) is selected from clothianidine, imidacloprid, thiamethoxam; and;
c) compound III (2) is selected from fipronil;
in synergistically effective amounts.

The present invention also relates to fivefold mixtures comprising the compound of formula I and four different compounds of formula II, or the compound of formula I, three different compounds of formula II and one further active compound III, or the compound of formula I, one compound of formula II and three further active compounds III, or, preferably, the compound of formula I, two different compounds of formula II and two further active compounds III, where compound III is as defined above, in synergistically effective amounts.

Preferably, the present invention also relates to fivefold mixtures comprising compound of formula I, two compounds II and two compounds III, wherein
 a) compound II (1) is selected from azoxystrobin, pyraclostrobin, trifloxystrobin and kresoxim-methyl; and
 b) compound II (2) is selected from fluopyram, fluxapyroxad, penflufen, penthiopyrad and sedaxane; and
 c) compound III (1) is selected from clothianidin, imidacloprid, thiamethoxam; and;
 d) compound III (2) is fipronil;
in synergistically effective amounts.

The terms "binary", "ternary", "quaternary" and "fivefold" in the above-defined binary, ternary, quaternary or fivefold mixtures refer to the number of active ingredients present in the mixture. "Active ingredient" in this context relates to a compound with an agriculturally relevant action, e.g. with a fungicidal, insecticidal, herbicidal or nematicidal activity.

The above-referred mixtures are hereinbelow also referred as "inventive mixtures".

The present invention also relates to a pesticidal (agricultural or veterinary) composition, comprising a liquid or solid carrier and a mixture as defined above.

The present invention furthermore relates to a method for increasing the health of plants, wherein the plant, the locus where the plant is growing or is expected to grow or plant propagation material from which the plant grows is treated with an effective amount of a compound of formula I.

Moreover, the invention relates to a method for controlling pests, wherein the pests, their habitat, breeding grounds, their food supply, their locus or the plants to be protected against pest attack, the soil or plant propagation material are treated with compound I in combination with at least one compound II in effective amounts, or, in other words, are treated with an effective amount of the mixture of the invention.

Additionally, the present invention also relates to a method for protection of plant propagation material and/or the plants which grow therefrom from pests comprising contacting the plant propagation material with compound I in combination with at least one compound II in effective amounts, or, in other words, contacting the plant propagation material with an inventive mixture in an effective amount. The invention also comprises plant propagation material treated with the inventive mixture.

The "combined" use of at least one compound I with the at least one compound II or the treatment according to the invention with the at least one compound I "in combination with" at least one compound II on the one hand can be understood as using a physical mixture of compound I and at least one compound II. On the other hand, the combined use may also consist in using compound I and the at least one compound II separately, but within a sufficiently short time of one another so that the desired effect can take place. More detailed illustrations of the combined use can be found in the specifications below.

The mixture of the invention has both a fungicidal activity as well as an activity against animal pests, especially an insecticidal activity. Thus, "pest" in the terms of the present invention relates both to phytopthogenic fungi and animal pests, e.g. invertebrate pests such as insects, arachnids, acarids or nematodes, in particular arthropod pests such as insects, arachnids or acarids, and especially insects.

Thus, in a preferred embodiment, the invention relates to a method for controlling phytopathogenic harmful fungi comprising contacting the phytopathogenic harmful fungi, their habitat, the plants, the soil, plant propagation material or materials to be protected against fungal attack with an effective amount of a mixture as defined above, or in other words, treating the phytopathogenic harmful fungi, their habitat, the plants, the soil, plant propagation material or materials to be protected against fungal attack with compound I in combination with at least one compound II in fungicidally effective amounts.

In an alternatively preferred embodiment, the invention relates to a method for controlling invertebrate pests which method comprises treating the pests, their food supply, their habitat or their breeding ground or a plant, plant propagation material, soil, area, material or environment in which the invertebrate pests are growing or may grow, or the materials, plants, plant propagation material, soils, surfaces or spaces to be protected from invertebrate pest attack or infestation with compound I in combination with at least one compound II in effective amounts, or, in other words, with an effective amount of the mixture of the invention.

In a preferred embodiment, the present invention also relates to a method for protection of plant propagation material and/or of the plants which grow therefrom from phytopathogenic harmful fungi comprising contacting the plant propagation materials with an inventive mixture in a fungicidally effective amount, or in other words, with compound I in combination with at least one compound II in fungicidally effective amounts. The invention also comprises plant propagation material treated with the inventive mixture.

In an alternatively preferred embodiment, the present invention also relates to a method for protection of plant propagation material from attack or infestation by invertebrate pests comprising contacting the plant propagation materials with an inventive mixture in an effective amount, or in other words, with compound I in combination with at least one compound II in effective amounts.

The present invention further provides a method for treating, controlling, preventing or protecting animals against infestation or infection by parasites which comprises orally, topically or parenterally administering or applying to the animals a parasiticidally effective amount of the mixture of the invention, or, in other words, administering or applying to the animals compound I in combination with compound II in parasiticidally effective amounts.

Additionally, in a further embodiment, the present invention also comprises a method for increasing the health of plants, said method comprising contacting the plant propagation materials of such plants with an inventive mixture in effective amounts, or in other words, with compound I in combination with at least one compound II in effective amounts. The invention also comprises plant propagation material treated with an inventive mixture.

The invention also relates to the use of the mixture of the invention for improving the health of plants.

The invention further relates to the use of the mixture of the invention for controlling pests.

The invention also relates to the use of a compound II for improving the pesticidal activity of compound I.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. In a particularly preferred embodiment, the term propagation material denotes seeds.

The present invention further relates to plant-protecting active ingredient mixtures having synergistically enhanced action of improving the health of plants and to a method for improving the health of plants and/or increasing the yield, wherein the plant, the locus where the plant is growing or is expected to grow or plant propagation material from which the plant grows is treated with an effective amount of an inventive mixture.

The compound of formula I, which has the IUPAC name [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cyclopropanecarboxylate as well as its pesticidal action has been described in WO2006/129714 and WO2009/081851, insecticidal mixtures thereof in WO2008/108491 and methods for producing the compound are for example disclosed in WO2009/022702.

The compounds II as well as their pesticidal action and methods for producing them are generally known. For instance, the commercially available compounds may be found in The Pesticide Manual, 14th Edition, British Crop Protection Council (2006) among other publications. Fluxapyroxad, bixafen, penflufen, penthiopyrad, isopyrazam and sedaxane are known as fungicides (cf., for example, EP-A 545 099, EP-A 589 301, EP-A 737682, EP-A 824099, WO 99/09013, WO 03/010149, WO 03/070705, WO 03/074491, WO 2004/005242, WO 2004/035589, WO 2004/067515, WO 06/087343,), or they can be prepared in the manner described therein.

Metalaxyl is a fungicide including: metalaxyl; metalaxyl consisting of equal or more than 50% by weight of the R-enantiomer and equal or less than 50% of the S-enantionmer; metalaxyl consisting of more than 85% by weight of the R-enantiomer less than 15% of the S-enantionmer; metalaxyl consisting of more than 92% by weight of the R-enantiomer and less than 8% of the S-enantionmer; metalaxyl consisting of more than 97% by weight of the R-enantiomer less than 3% of the S-enantionmer; and mefenoxam (i.e., more than 97.5% R-metalaxyl or metalaxyl-M and less than 2.5% of the S-enantionmer). See, for example, the Pesticide Manual, 11th Ed. (1997), The British Crop Protection Council, London, page 792; and the Pesticide Manual, 11th Ed. (1997), The British Crop Protection Council, London, page 794.

References for the biological control agents of Group Z) are set forth below: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bioferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. Endothia parasitica from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone Biolnnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIOCURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from BotryZen Ltd, NZ).

One typical problem arising in the field of pest control lies in the need to reduce the dosage rates of the active ingredient in order to reduce or avoid unfavorable environmental or toxicological effects whilst still allowing effective pest control.

The term "phytopathogenic harmful fungi" is hereinbelow also abbreviated as "harmful fungi".

Another problem encountered concerns the need to have available pest control agents which are effective against a broad spectrum of harmful fungi.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of harmful fungi, which have developed natural or adapted resistance against the active compound in question. Therefore there is a need for pest control agents that help prevent or overcome resistance.

Another problem underlying the present invention is the desire for compositions that improve plants, a process which is commonly and hereinafter referred to as "plant health".

The term plant health comprises various sorts of improvements of plants that are not connected to the control of pests. For example, advantageous properties that may be mentioned are improved crop characteristics including: emergence, crop yields, protein content, oil content, starch content, more developed root system (improved root growth), improved stress tolerance (e.g. against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination; or any other advantages familiar to a person skilled in the art.

If used in connection with the treatment of plant propagation material (preferably seeds) the term "plant health" is equivalent with "seed vitality". Seed vitality manifests itself in a variety of factors. Examples of factors which are manifestations of the plant's vitality are:
(a) overall visual appearance;
(b) root growth and/or root development;
(c) size of the leaf area;
(d) intensity of the leaves' green coloration;
(e) number of dead leaves in the vicinity of the ground;
(f) plant height;
(g) plant weight;
(h) growth rate;
(i) plant stand density;
(j) germination behavior;
(k) emergence behavior;
(l) shoot number;
(m) shoot type (quality and productivity)
(n) toughness of the plant, for example resistance to biotic or abiotic stress;
(o) presence of necroses;
(p) senescence behavior.

Preferably, the term "Seed vitality" denotes plant stand density, storability of seeds and/or germination behavior.

A further object of various efforts in crop protection is to increase the yield of plants. "Yield" is to be understood as any plant product of economic value that is produced by the plant such as grains, fruits in the proper sense, vegetables, nuts, grains, seeds, wood (e.g. in the case of silviculture plants) or even flowers (e.g. in the case of gardening plants, ornamentals). The plant products may in addition be further utilized and/or processed after harvesting.

According to the present invention, "increased yield" of a plant, in particular of an agricultural, silvicultural and/or horticultural plant, preferably agricultural plant means that the yield of a product of the respective plant is increased by a measurable amount over the yield of the same product of the plant produced under the same conditions, but without the application of the mixture according to the invention.

Increased yield can be characterized, among others, by following improved properties of the plant:
increased plant weight
increased plant height
increased biomass such as higher overall fresh weight (FW)
higher grain yield
more tillers
larger leaves
increased shoot growth
increased protein content
increased oil content
increased starch content
increased pigment content.

According to the present invention, the yield is increased by at least 2%, preferable by at least 4%, more preferred by at least 8%, even more preferred by at least 16%.

It has to be emphasized that the above effects of the mixture of the invention or of compound I when used alone, i.e. enhanced crop yield of the plant, also are present when the plant is not under biotic stress and in particular when the plant is not under pest pressure, such as fungi or insect stress. It is evident that a plant suffering from pest attack produces a smaller biomass and a smaller crop yield as compared to a plant which has been subjected to curative or preventive treatment against the pest and which can grow without the damage caused by the biotic stress factor. However, the use and the method according to the invention lead to an enhanced crop yield even in the absence of any biotic stress and in particular in the absence of any pest. This means that the positive effect of the mixture of the invention or of compound I used alone on the crop yield cannot be explained just by the pesticidal activities of the mixture, but is based on further activity profiles. But of course, plants under biotic stress can be treated, too, according to the methods of the present invention.

EP 2119361 and EP 2223599 disclose several pesticidal mixtures which may, inter alia, comprise the compound of formula I.

However, the outstanding synergistic fungicidal and/or plant health action of the specific inventive mixtures as well as the as defined at the outset are not disclosed therein, also not, that such combinations might have and especially its suitability for seed treatment purposes.

It was therefore an object of the present invention to provide pesticidal mixtures which solve the problems of reducing the dosage rate and/or enhancing the spectrum of activity and/or combining knock-down activity with prolonged control and/or to resistance management and/or promoting the health of plants.

It was also an object of the present invention to provide methods of increasing the health of plants.

We have found that this object is in part or in whole achieved by the complex mixtures comprising the active compounds defined in the outset.

Herein, we have found a method for increasing the health of plants, wherein the plant, the locus where the plant is growing or is expected to grow or plant propagation material from which the plant grows is treated with an effective amount of a compound of formula I, wherein preferably the plant propagation material from which the plant grows is treated with an effective amount of a compound of formula I. Such latter treatment of plant propagation material leads to increase in seed vitality.

It has been found that the mixtures as defined in the outset show markedly enhanced action against harmful pests, such as harmful fungi or animal pests, preferably harmful fungi, compared to the control rates that are possible with the individual compounds and/or is suitable for improving the health of plants when applied to plants, parts of plants, plant propagation materials (preferably seeds), or at their locus of growth.

It has been found that the action of the inventive mixtures goes far beyond the pesticidal, such as fungicidal or insecticidal, preferably fungicidal, and/or plant health improving action of the active compounds present in the mixture alone (synergism).

In particular, it has been found that the action of the inventive mixtures goes far beyond the pesticidal, such as fungicidal or insecticidal, preferably fungicidal, and/or plant health improving action of the active compounds present in the mixture alone (synergism) if applied as a seed treatment.

These mixtures are also suitable for improving the health of plants when applied to plants, parts of plants, seeds, or at their locus of growth, preferably to plants and plant propagation material, more preferably to seeds.

Moreover, we have found that simultaneous, that is joint or separate, application of the compound I and compound II or successive application of the compound I and compound II allows enhanced control of harmful pests, such as harmful fungi or animal pests, preferably harmful fungi, compared to the control rates that are possible with the individual compounds (synergistic mixtures).

Moreover, we have found that simultaneous, that is joint or separate, application of the compound I and compound II or successive application of the compound I and compound II provides enhanced plant health effects compared to the plant health effects that are possible with the individual compounds (synergistic mixtures wherein the synergism is plant health synergism).

In general, the overall ratios by weight for the respective mixtures comprising the compound I and the at least one compound II are from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

In a preferred embodiment, the present invention relates to synergistic mixtures comprising,
1) the insecticidal compound of formula I

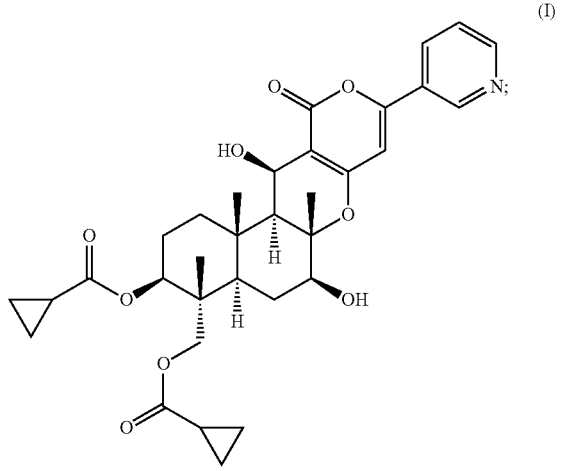

(I)

and
2) one or more, e.g. 1, 2, 3 or 4, specifically one fungicidal compound II selected from the compounds of following groups A to Ab:
A) strobilurin fungicides selected from the group consisting of coumethoxystrobin, coumoxystrobin, dimoxystrobin, enestroburin, metominostrobin, pyraclostrobin, pyrametostrobin, pyraoxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide;
B) carboxanilides selected from the group consisting of fluxapyroxad, bixafen, penflufen, sopyrazam, sedaxane, benodanil, carboxin, fenfuram, fenhexamid, furametpyr, kiralaxyl, oxycarboxin, tecloftalam, thifluzamide, 2-amino-4-methyl-thiazole-5-carboxanilide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide;
C) carboxylic morpholides selected from the group consisting of flumorph, and pyrimorph;
Cc) benzimidazoles or benzimidazole releasing precursors selected from the group consisting of debacarb and furophanate;
D) benzoic acid amides selected from the group consisting of flumetover, fluopyram, zoxamide;
E) carboxamides selected from the group consisting of mandiproamid, oxytetracyclin, silthiofam and N-(6-methoxy-pyridin-3-yl)cyclopropanecarboxylic acid amide;
F) azole fungicides, such group selected from the group consisting of the triazoles fungicides azaconazole, bromuconazole, difenoconazole, diniconazole, diniconazole-M, epoxiconazole, fenbuconazole, fluquinconazole, flutriafol, imibenconazole, ipconazole, metconazole, oxpoconazole, paclobutrazole, prothioconazole, tetraconazole, triadimenol, triticonazole, uniconazole; of the
imidazole fungicides imazalil, pefurazoate;
and of the azoles ethaboxam, etridiazole, hymexazole and 2-(4-chloro-phenyl)-N-[4-(3,4-dimethoxy-phenyl)-isoxazol-5-yl]-2-prop-2-ynyloxy-acetamide;
G) pyridines selected from the group consisting of 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;
H)—pyrimidines selected from the group consisting of bupirimate, diflumetorim, nitrapyrin, nuarimol;
K) morpholines selected from the group consisting of aldimorph, dodemorph, dodemorph-acetate, tridemorph; o
M) dicarboximides selected from the group consisting of fluoroimid;
N) non-aromatic 5-membered heterocycles selected from the group consisting of flutianil, octhilinone, 5-amino-2-isopropyl-3-oxo-4-ortho-tolyl-2,3-dihydro-pyrazole-1-carbothioic acid S-allyl ester;
O) fungicides selected from the group consisting of ametoctradin, amisulbrom, anilazin, blasticidin-S, chinomethionat, dazomet, diclomezine, difenzoquat, difenzoquat-methylsulfate, oxolinic acid, piperalin, triazoxide, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo[1,5-a]pyrimidine;
P) thio- and dithiocarbamates selected from the group consisting of ferbam, metam, methasulphocarb, metiram, thiram and ziram;
Q) carbamates selected from the group consisting of propamocarb, propamocarb hydrochlorid, valifenalate and N-(1-(1-(4-cyano-phenyl)ethanesulfonyl)-but-2-yl)carbamic acid-(4-fluorophenyl)ester;
R) guanidine fungicides selected from the group consisting of guanidine, dodine, dodine free base, guazatine, guazatine-acetate, iminoctadine, iminoctadine-triacetate and iminoctadine-tris(albesilate); or from S) antibiotic fungicides selected from the group consisting of streptomycin, polyoxine;

T) nitrophenyl derivates selected from the group consisting of binapacryl, dicloran, dinobuton, dinocap, nitrothal-isopropyl and tecnazen, U) organometal compounds selected from the group consisting of fentin salts, such as fentin-acetate, fentin chloride or fentin hydroxide;

V) sulfur-containing heterocyclyl compounds consisting of dithianon, isoprothiolane;

W) organophosphorus compounds selected from the group consisting of edifenphos, iprobenfos, phosphorous acid and its salts, pyrazophos;

X) organochlorine compounds selected from the group consisting of dichlorophen, flusulfamide, hexachlorobenzene, pentachlorphenole and its salts, tolylfluanid, N-(4-chloro-2-nitro-phenyl)-N-ethyl-4-methylbenzenesulfonamide;

Y) —inorganic active substances selected from the group consisting of Bordeaux mixture, copper acetate, copper oxychloride, basic copper sulfate, sulfur;

Z) antifungal biocontrol agents, plant bioactivators selected from the group consisting of *Ampelomyces quisqualis, Aspergillus flavus, Aureobasidium pullulans, Bacillus pumilus, Bacillus subtilis, Bacillus subtilis* var. *amyloliquefaciens* FZB24, *Candida oleophila* I-82, *Candida saitoana, Clonostachys rosea* f. *catenulata*, also named *Gliocladium catenulatum Coniothyrium minitans, Cryphonectria parasitica, Cryptococcus albidus, Fusarium oxysporum, Metschnikowia fructicola, Microdochium dimerum, Phlebiopsis gigantea, Pseudozyma flocculosa, Pythium oligandrum* DV74, *Reynoutria sachlinensis, Talaromyces flavus* V117b, *Trichoderma asperellum* SKT-1, *T. atroviride* LC52, *T. harzianum* T-22, *T. harzianum* TH 35, *T. harzianum* T-39, *T. harzianum* and *T. viride, T. harzianum* ICC012 and *T. viride* ICC080, *T. polysporum* and *T. harzianum, T. stromaticum, T. virens* GL-21, *T. viride, T. viride* TV1, *Uloclardium oudemansii* HRU3; and Ab) fungicides selected from the group consisting of biphenyl, bronopol, diphenylamin, metrafenone, pyriofenone, mildiomycin, oxin-copper, prohexadione-calcium, spiroxamine, tebufloquin, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethylphenyl)-N-ethyl-N-methyl formamidine, N'-(4-(4-fluoro-3-trifluoromethyl-phenoxy)-2,5-dimethylphenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-ylester and N-Methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide;

in synergistic effective amounts.

Suitable and preferred weight ratios of compound I and compound(s) II are listed above.

Alternatively, preference is given to mixtures comprising compound I and as fungicidal compound II at least one fungicide selected from the strobilurines of group A), and particularly selected from the strobilurines azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb and trifloxystrobin, more preferably azoxystrobin, dimoxystrobin, enestroburin, fluoxastrobin, kresoxim-methyl, metominostrobin, orysastrobin, picoxystrobin, pyraclostrobin, pyribencarb and trifloxystrobin in synergistically effective amounts, preferably in a ratio by weight of compound I:II from 1:500 to 1500:1, preferably from 1:100 to 1000:1, more preferably from 1:25 to 500:1, even more preferably from 1:10 to 100:1, and in particular from 1:1 to 100:1, e.g. 1:10 to 100:1 or 1:20 to 100:1. Even more preference is given to mixtures comprising compound I and as fungicidal compound II at least one fungicide selected from the strobilurines of group A), which are in turn selected from the strobilurines dimoxystrobin, enestroburin, metominostrobin and pyraclostrobin, in synergistically effective amounts, preferably in a ratio by weight of compound I:II from 1:500 to 1500:1, preferably from 1:100 to 1500:1, more preferably from 1:25 to 1000:1, even more preferably from 1:10 to 500:1, and in particular from 1:1 to 100:1, e.g. 10:1 to 100:1 or 20:1 to 100:1. Specifically, the strobilurin fungicide is pyraclostrobin.

Alternatively, preference is given to mixtures comprising compound I and as fungicidal compound II at least one fungicide selected from the carboxamides of group B), and particularly selected from bixafen, boscalid, fluxapyroxad, isopyrazam, penflufen, penthiopyrad, sedaxane, metalaxyl and ofurace in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1. More preference is given to mixtures comprising compound I and as fungicidal compound II at least one fungicide selected from the carboxamides of group B), which are preferably selected from bixafen, fluxapyroxad, isopyrazam, penflufen and sedaxane in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1. Specifically, the carboxamide fungicide is fluxapyroxad.

Preference is also given to mixtures comprising compound I and as fungicidal compound II at least one fungicide selected from group C) or D), and particularly selected from dimethomorph, flumorph, fluopicolid (picobenzamid) and zoxamide in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II at least one fungicide selected from group C) or D), which are selected from flumorph and zoxamide in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group E), and particularly selected from carpropamid and mandipropamid in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II mandipropamid in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising a compound of formula I and as fungicidal compound II at least one fungicide selected from the group of azoles F), and particularly selected from the azoles cyproconazole, difenoconazole, epoxiconazole, fluquinconazole, flusilazole, flutriafol, hymexazole, ipconazole, imazalil, metconazole, myclobutanil, penconazole, propiconazole, prothioconazole, triadimefon, triadimenol, tebuconazole, tetraconazole, triticonazole, prochloraz, cyazofamid, and ethaboxam in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising a compound of formula I and as fungicidal compound II at least one fungicide selected from the group of azoles F), which are selected from the azoles difenoconazole, epoxiconazole, fluquinconazole, flutriafol, hymexazole, ipconazole, imazalil, metconazole, prothioconazole, triadimenol, tetraconazole, triticonazole, cyazofamid, and ethaboxam in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group G), and particularly selected from fluazinam in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group H), and particularly selected from cyprodinil, fenarimol, mepanipyrim, pyrimethanil in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and triforine in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and fludioxonil in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and at least one fungicidal compound II selected from the group of morpholines, in particular of dodemorph, fenpropimorph or tridemorph. More preference is also given to mixtures comprising compound I and at least one fungicidal compound II selected from the group of morpholines, which are selected from dodemorph and tridemorph.

Preference is also given to mixtures comprising compound I and silthiofam in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group M), and particularly selected from iprodione and vinclozolin in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group N), and particularly selected from famoxadone, fenamidone and probenazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group 0), and particularly selected from acibenzolar-S-methyl, captafol, folpet, fenoxanil, quinoxyfen and ametoctradin in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II ametoctradin in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group P), and particularly selected from mancozeb, metiram, propineb and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1. More reference is given to mixtures comprising compound I and as fungicidal compound II at least one fungicide selected from group P), which is selected from metiram, and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group Q), and particularly selected from iprovalicarb, benthiavalicarb and propamocarb in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II propamocarb in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and dithianon in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group U), and particularly selected from the fentin salts, such as fentin acetate in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group W), and particularly selected from fosetyl, fosetyl-aluminium, phosphorous acid and salts thereof in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II phosphorous acid and salts thereof in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group X), and particularly selected from chlorthalonil and dichlofluanid in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group Y), and particularly selected from copper acetate, copper hydroxide, copper oxychloride, copper sulfate and sulfur in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II at least one fungicide selected from group Y), and particularly selected from copper acetate, copper oxychloride, copper sulfate and sulfur in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and as fungicidal compound II at least one fungicide selected from group Ab), and particularly selected from cymoxanil, metrafenone, spiroxamine and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide in synergistically effective amounts, preferably in a ratio by weight of compound I:II from 1:500 to 500:1, preferably from 1:100 to 100:1, more preferably from 1:25 to 25:1 and most preferably from 1:10 to 10:1. More preference is given to mixtures comprising compound I and as fungicidal compound II at least one fungicide selected from group Ab), which is selected from metrafenone, spiroxamine and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Preference is also given to mixtures comprising compound I and at least one active substance selected from the antifungal biocontrol agents given in group Z) and particularly selected from *Bacillus subtilis* strain NRRL No. B-21661, *Bacillus pumilus* strain NRRL No. B-30087 and *Ulocladium oudemansii* in synergistically effective amounts.

Preference is also given to mixtures comprising compound I and as fungicidal compound II at least one fungicide selected from group Cc), and particularly selected from thiophanate-methyl, benomyl, carbendazim and thiabendazol in synergistically effective amounts, preferably in a ratio by weight of compound I:II from 1:500 to 500:1, preferably from 1:100 to 100:1, more preferably from 1:25 to 25:1 and most preferably from 1:10 to 10:1.

As mentioned at the outset, the inventive mixtures are in a preferred embodiment used as a seed treatment. For the purpose of seed treatment, the following mixtures are preferred:

Mixtures comprising compound I and as fungicidal compound II at least one fungicide selected from the strobilurines azoxystrobin, dimoxystrobin, fluoxastrobin, kresoxim-methyl, orysastrobin, picoxystrobin, pyraclostrobin, and trifloxystrobin, more preferably from dimoxystrobin and pyraclostrobin, in particular pyraclostrobin, in synergistically effective amounts, preferably in a ratio by weight of compound I:II from 1:500 to 1500:1, preferably from 1:100 to 1000:1, more preferably from 1:25 to 500:1, an even more preferably from 1:10 to 100:1, and in particular from 1:1 to 100:1, e.g. 10:1 to 100:1 or 20:1 to 100:1.

Mixtures comprising compound I and as fungicidal compound II at least one carboxamide fungicide selected from bixafen, boscalid, fluopyram, fluxapyroxad, isopyrazam, penflufen, penthiopyrad and sedaxane, more preferably from bixafen, fluxapyroxad, isopyrazam, penflufen and sedaxane, in particular fluxapyroxade, in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

Mixtures comprising a compound of formula I and at least one azole fungicide selected from the azoles cyproconazole, difenoconazole, epoxiconazole, fluquinconazole, flutriafol, hymexazole, ipconazole, imazalil, metconazole, prothioconazole, tebuconazole, triticonazole, prochloraz and pyrimethanil, preferably from difenoconazole, epoxiconazole, fluquinconazole, flutriafol, hymexazole, ipconazole, imazalil, metconazole, prothioconazole and triticonazole, in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising a compound of formula I and at least one fungicide selected from fludioxonil, silthiofam, iprodione, metiram and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and at least one active substance selected from the antifungal biocontrol agents *Bacillus subtilis* strain NRRL No. B-21661, *Bacillus pumilus* strain NRRL No. B-30087 and *Ulocladium oudemansii* in synergistically effective amounts.

Mixtures comprising compound I and as fungicidal compound II at least one benzimidazole or benzimidazole releasing precursor fungicide selected from thiophanate-methyl, benomyl, carbendazim, and thiabendazol in synergistically effective amounts, preferably in a ratio by weight of compound I:II from 1:500 to 500:1, preferably from 1:100 to 100:1, more preferably from 1:25 to 25:1 and most preferably from 1:10 to 10:1.

For the purpose of seed treatment, the following mixtures are more preferred:

Mixtures comprising compound I and as fungicidal compound II a fungicide selected from the strobilurines azoxystrobin, kresoxim-methyl, orysastrobin, picoxystrobin, pyraclostrobin, and trifloxystrobin, more preferably from dimoxystrobin and pyraclostrobin, in particular pyraclostrobin, in synergistically effective amounts, preferably in a ratio by weight of compound I:II from 1:500 to 1500:1, preferably from 1:100 to 1000:1, more preferably from 1:25 to 500:1, even more preferably from 1:10 to 100:1, and in particular from 1:1 to 100:1, e.g. 10:1 to 100:1 or 20:1 to 100:1.

Mixtures comprising compound I and as fungicidal compound II a carboxamide fungicide selected from boscalid, fluopyram, fluxapyroxad, penflufen, penthiopyrad and sedaxane, more preferably from bixafen, fluxapyroxad, isopyrazam, penflufen and sedaxane, in particular fluxapyroxad, in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

Mixtures comprising a compound of formula I and an azole fungicide selected from the azoles cyproconazole, difenoconazole, epoxiconazole, fluquinconazole, flutriafol, hymexazole, ipconazole, imazalil, metconazole, prothioconazole, tebuconazole, triticonazole, prochloraz and pyrimethanil, preferably from difenoconazole, epoxiconazole, fluquinconazole, flutriafol, hymexazole, ipconazole, imazalil, metconazole, prothioconazole and triticonazole, in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising a compound of formula I and a fungicide selected from fludioxonil, silthiofam, iprodione, metiram and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and at least one active substance selected from the antifungal biocontrol agents *Bacillus subtilis* strain NRRL No. B-21661, *Bacillus pumilus* strain NRRL No. B-30087 and *Ulocladium oudemansii* in synergistically effective amounts.

Mixtures comprising compound I and as fungicidal compound II a benzimidazoles or benzimidazole releasing precursor fungicide selected from thiophanate-methyl, benomyl, carbendazim, and thiabendazol in synergistically effective amounts, preferably in a ratio by weight of compound I:II from 1:500 to 500:1, preferably from 1:100 to 100:1, more preferably from 1:25 to 25:1 and most preferably from 1:10 to 10:1.

For the purpose of seed treatment, the following mixtures are most preferred:

Mixtures comprising compound I and azoxystrobin in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and pyraclostrobin in synergistically effective amounts, preferably in a ratio by weight of compound I:II from 1:500 to 500:1, preferably from 1:100 to 100:1, more preferably from 1:25 to 100:1, even more preferably from 1:10 to 100:1, and in particular from 1:1 to 100:1, e.g. 10:1 to 100:1 or 20:1 to 100:1.

Mixtures comprising compound I and trifloxystrobin in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and kresoxim-methyl in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and boscalid in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and fluopyram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and fluxapyroxad in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

Mixtures comprising compound I and penflufen in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and penthiopyrad in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and sedaxane in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and fluquinconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and ipconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and prothioconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and tebuconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and triticonazole in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and prochloraz in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and fludioxonil in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and silthiofam in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and iprodione in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and thiophanate-methyl in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and carbendazim in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and metalaxyl in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and dimethomorph in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and difenoconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Utmost preference for the purpose of seed treatment is given to the following mixtures:

Mixtures comprising compound I and pyraclostrobin in synergistically effective amounts, preferably in a ratio by weight of compound I:II from 1:500 to 500:1, preferably from 1:100 to 100:1, more preferably from 1:25 to 100:1, even preferably from 1:10 to 100:1, and in particular from 1:1 to 100:1, e.g. 10:1 to 100:1 or 20:1 to 100:1.

Mixtures comprising compound I and fluopyram in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and fluxapyroxad in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

Mixtures comprising compound I and penflufen in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and sedaxane in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and fluquinconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and ipconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and prothioconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and tebuconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and triticonazole in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and silthiofam in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and thiram in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and carbendazim in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and metalaxyl in synergistically effective amounts, preferably in a ratio by weight of compound I:II from 1:500 to 500:1, preferably from 1:100 to 100:1, more preferably from 1:25 to 25:1 and most preferably from 1:10 to 10:1

Mixtures comprising compound I and dimethomorph in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Mixtures comprising compound I and difenoconazole in synergistically effective amounts, preferably in a ratio by weight of compound I:II from 1:500 to 500:1, preferably from 1:100 to 100:1, more preferably from 1:25 to 25:1 and most preferably from 1:10 to 10:1.

Among the above mixture, specific preference is given to following mixtures:

Mixtures comprising compound I and pyraclostrobin in synergistically effective amounts, preferably in a ratio by weight of compound I:II from 1:500 to 500:1, preferably from 1:100 to 100:1, more preferably from 1:25 to 100:1, even preferably from 1:10 to 100:1, and in particular from 1:1 to 100:1, e.g. 10:1 to 100:1 or 20:1 to 100:1; and mixtures comprising compound I and fluxapyroxad in synergistically effective amounts, preferably in a ratio by weight of compound I:II from 1:500 to 1500:1, preferably from 1:100 to 1500:1, more preferably from 1:25 to 1500:1, even more preferably from 1:10 to 1500:1, and in particular from 1:1 to 1500:1, e.g. 10:1 to 1200:1 or 20:1 to 1100:1.

In a preferred embodiment the present invention also relates to ternary mixtures comprising the compound of formula I and two compounds II, wherein compounds II are selected from thiophanate-methyl, metalaxyl, azoxystrobin, pyraclostrobin, trifloxystrobin, prochloraz, fludioxonil, dimethomorph, triticonazole, difenoconazole, kresoxim-methyl, boscalid, fluopyram, fluxapyroxad, penflufen, penthiopyrad, sedaxane and pyrimethanil in synergistically effective amounts.

With respect to their intended use as a seed treatment, the following ternary mixtures of compound I and two fungicidal compounds II set forth below in table 1 are preferred.

The ratios by weight for the respective tertiary mixtures of compound I, and first compound II and second compound II are preferably from 1:100:100 to 100:1:1, more preferably from 50:1:1 to 1:50:50, even more preferably from 1:20:20 to 20:1:1.

In table 1, the following abbreviations are used herein:
I is compound I bos=boscalid
II is compound II Fluo=fluopyram
TPM=thiophanate-methyl Fluoxa=fluxapyroxad
Meta=metalaxyl Pen=penflufen
Azox=azoxystrobin Penthio=penthiopyrad
Pyra=pyraclostrobin Seda=sedaxane
Trifl=trifloxystrobin Pyri=pyrimethanil
Pz=prochloraz CP-I=compound of formula I
Flu=fludioxonil
DMM=dimethomorph
TTZ=Triticonazole
Difeno=Difenoconazole
KM=Kresoxim-methyl

TABLE 1

| No | I | II (1) | II (2) |
|---|---|---|---|
| R-1 | CP-I | TPM | Meta |
| R-2 | CP-I | TPM | Azox |
| R-3 | CP-I | TPM | Pyra |
| R-4 | CP-I | TPM | Trifl |
| R-5 | CP-I | TPM | Pz |
| R-6 | CP-I | TPM | Flu |
| R-7 | CP-I | TPM | DMM |
| R-8 | CP-I | TPM | bos |
| R-9 | CP-I | TPM | Fluo |
| R-10 | CP-I | TPM | Fluoxa |
| R-11 | CP-I | TPM | Pen |
| R-12 | CP-I | TPM | Penthio |
| R-13 | CP-I | TPM | Seda |
| R-14 | CP-I | TPM | Pyri |
| R-15 | CP-I | Azox | Pyra |
| R-16 | CP-I | Azox | Trifl |
| R-17 | CP-I | Azox | Pz |
| R-18 | CP-I | Azox | Flu |
| R-19 | CP-I | Azox | DMM |
| R-20 | CP-I | Azox | bos |
| R-21 | CP-I | Azox | Fluo |
| R-22 | CP-I | Azox | Fluoxa |
| R-23 | CP-I | Azox | Pen |
| R-24 | CP-I | Azox | Penthio |
| R-25 | CP-I | Azox | Seda |
| R-26 | CP-I | Azox | Pyri |
| R-27 | CP-I | Pyra | Trifl |
| R-28 | CP-I | Pyra | Pz |
| R-29 | CP-I | Pyra | Flu |
| R-30 | CP-I | Pyra | DMM |
| R-31 | CP-I | Pyra | bos |
| R-32 | CP-I | Pyra | Fluo |
| R-33 | CP-I | Pyra | Fluoxa |
| R-34 | CP-I | Pyra | Pen |
| R-35 | CP-I | Pyra | Penthio |
| R-36 | CP-I | Pyra | Seda |
| R-37 | CP-I | Pyra | Pyri |
| R-38 | CP-I | Trifl | Pz |
| R-39 | CP-I | Trifl | Flu |
| R-40 | CP-I | Trifl | DMM |
| R-41 | CP-I | Trifl | bos |
| R-42 | CP-I | Trifl | Fluo |
| R-43 | CP-I | Trifl | Fluoxa |
| R-44 | CP-I | Trifl | Pen |
| R-45 | CP-I | Trifl | Penthio |
| R-46 | CP-I | Trifl | Seda |
| R-47 | CP-I | Trifl | Pyri |
| R-48 | CP-I | Pz | Flu |
| R-49 | CP-I | Pz | DMM |
| R-50 | CP-I | Pz | bos |
| R-51 | CP-I | Pz | Fluo |
| R-52 | CP-I | Pz | Fluoxa |
| R-53 | CP-I | Pz | Pen |
| R-54 | CP-I | Pz | Penthio |
| R-55 | CP-I | Pz | Seda |
| R-56 | CP-I | Pz | Pyri |
| R-57 | CP-I | Flu | DMM |
| R-58 | CP-I | Flu | bos |
| R-59 | CP-I | Flu | Fluo |
| R-60 | CP-I | Flu | Fluoxa |
| R-61 | CP-I | Flu | Pen |
| R-62 | CP-I | Flu | Penthio |
| R-63 | CP-I | Flu | Seda |
| R-64 | CP-I | Flu | Pyri |
| R-65 | CP-I | DMM | bos |
| R-66 | CP-I | DMM | Fluo |
| R-67 | CP-I | DMM | Fluoxa |
| R-68 | CP-I | DMM | Pen |
| R-69 | CP-I | DMM | Penthio |
| R-70 | CP-I | DMM | Seda |
| R-71 | CP-I | DMM | Pyri |
| R-72 | CP-I | bos | Fluo |
| R-73 | CP-I | bos | Fluoxa |
| R-74 | CP-I | bos | Pen |
| R-75 | CP-I | bos | Penthio |
| R-76 | CP-I | bos | Seda |
| R-77 | CP-I | bos | Pyri |
| R-78 | CP-I | Fluo | Fluoxa |
| R-79 | CP-I | Fluo | Pen |
| R-80 | CP-I | Fluo | Penthio |
| R-81 | CP-I | Fluo | Seda |
| R-82 | CP-I | Fluo | Pyri |
| R-83 | CP-I | Fluoxa | Pen |
| R-84 | CP-I | Fluoxa | Penthio |
| R-85 | CP-I | Fluoxa | Seda |
| R-86 | CP-I | Fluoxa | Pyri |

TABLE 1-continued

| No | I | II (1) | II (2) |
|---|---|---|---|
| R-87 | CP-I | Pen | Penthio |
| R-88 | CP-I | Pen | Seda |
| R-89 | CP-I | Pen | Pyri |
| R-90 | CP-I | Penthio | Seda |
| R-91 | CP-I | Penthio | Pyri |
| R-92 | CP-I | Seda | Pyri |
| R-93 | CP-I | Triti | Meta |
| R-94 | CP-I | Triti | Azox |
| R-95 | CP-I | Triti | Pyra |
| R-96 | CP-I | Triti | Trifl |
| R-97 | CP-I | Triti | Pz |
| R-98 | CP-I | Triti | Flu |
| R-99 | CP-I | Triti | DMM |
| R-100 | CP-I | Triti | bos |
| R-101 | CP-I | Triti | Fluo |
| R-102 | CP-I | Triti | Fluoxa |
| R-103 | CP-I | Triti | Pen |
| R-104 | CP-I | Triti | Penthio |
| R-105 | CP-I | Triti | Seda |
| R-106 | CP-I | Triti | Pyri |
| R-107 | CP-I | Triti | KM |
| R-108 | CP-I | Triti | Difeno |
| R-109 | CP-I | KM | Azox |
| R-110 | CP-I | KM | Pyra |
| R-111 | CP-I | KM | Trifl |
| R-112 | CP-I | KM | Pz |
| R-113 | CP-I | KM | Flu |
| R-114 | CP-I | KM | DMM |
| R-115 | CP-I | KM | bos |
| R-116 | CP-I | KM | Fluo |
| R-117 | CP-I | KM | Fluoxa |
| R-118 | CP-I | KM | Pen |
| R-119 | CP-I | KM | Penthio |
| R-120 | CP-I | KM | Seda |
| R-121 | CP-I | KM | Pyri |
| R-122 | CP-I | KM | Difeno |
| R-123 | CP-I | Difeno | Azox |
| R-124 | CP-I | Difeno | Pyra |
| R-125 | CP-I | Difeno | Trifl |
| R-126 | CP-I | Difeno | Pz |
| R-127 | CP-I | Difeno | Flu |
| R-128 | CP-I | Difeno | DMM |
| R-129 | CP-I | Difeno | bos |
| R-130 | CP-I | Difeno | Fluo |
| R-131 | CP-I | Difeno | Fluoxa |
| R-132 | CP-I | Difeno | Pen |
| R-133 | CP-I | Difeno | Penthio |
| R-134 | CP-I | Difeno | Seda |
| R-135 | CP-I | Difeno | Pyri |

In a preferred embodiment the present invention also relates to ternary mixtures comprising compound of formula I, compound II and compound III, wherein
  a) compound II is selected from azoxystrobin, pyraclostrobin, trifloxystrobin, kresoxim-methyl, fluopyram, fluxapyroxad, penflufen, penthiopyrad and sedaxane; and
  b) compound III is selected from clothianidine, imidacloprid, thiamethoxam and fipronil;
  in synergistically effective amounts.

In a preferred embodiment the present invention also relates to quarternary mixtures comprising compound of formula I, compound II and two compounds III, wherein
  a) compound II is selected from azoxystrobin, pyraclostrobin, trifloxystrobin, kresoxim-methyl, fluopyram, fluxapyroxad, penflufen, penthiopyrad and sedaxane; and
  b) compound III (1) is selected from clothianidine, imidacloprid, thiamethoxam; and;
  c) compound III (2) is fipronil;
  in synergistically effective amounts.

In a preferred embodiment the present invention also relates to fivefold mixtures comprising compound of formula I, two compounds II and two compounds III, wherein
  a) compound II (1) is selected from azoxystrobin, pyraclostrobin, trifloxystrobin and kresoxim-methyl; and
  b) compound II (2) is selected from fluopyram, fluxapyroxad, penflufen, penthiopyrad and sedaxane; and
  c) compound III (1) is selected from clothianidine, imidacloprid, thiamethoxam; and;
  d) compound III (2) is selected from fipronil;
  in synergistically effective amounts.

The ratios by weight for the respective tertiary mixtures of compound I, and one compound II and a further compound III are preferably from 1:100:100 to 100:1:1, more preferably from 50:1:1 to 1:50:50, even more preferably from 1:20:20 to 20:1:1.

The ratios by weight for the respective quarternary mixtures comprising compound I, and one compound II and two further compounds III are preferably from 1:100:100:100 to 100:1:1:1, more preferably from 50:1:1:1 to 1:50:50:50, even more preferably from 1:20:20:20 to 20:1:1:1.

The ratios by weight for the respective quarternary mixtures comprising compound I, and two compounds II and one further compounds III are preferably from 1:100:100:100 to 100:1:1:1, more preferably from 50:1:1:1 to 1:50:50:50, even more preferably from 1:20:20:20 to 20:1:1:1.

The ratios by weight for the respective fivefold mixtures comprising compound I, two compounds II and two compounds III and an insecticide IV (I:II:II:III:III) are preferably from 1:100:100:100:100 to 100:1:1:1:1, more preferably 50:1:1:1:1 to 1:50:50:50:50, even more preferably 1:20:20:20:20 to 20:1:1:1:1.

With respect to their intended use as a seed treatment, the following mixtures set forth below in table 2 are preferred.

In table 2, the following abbreviations are used herein:
I is compound I Fluo=fluopyram
II is compound II Fluoxa=fluxapyroxad
III is compound III Pen=penflufen
Azox=azoxystrobin Penthi=penthiopyrad
Pyra=pyraclostrobin Seda=sedaxane
Trifl=trifloxystrobin CP-I=compound of formula I
KM=Kresoxim-methyl Fip=Fipronil
Clo=clothianidine
Imi=imidacloprid
TMX=thiamethoxam

TABLE 2

| No | I | II (1) | II (1) | III (1) | IV (2) |
|---|---|---|---|---|---|
| R-136 | CP-I | Pyra | — | Fip | — |
| R-137 | CP-I | Pyra | — | Clo | — |
| R-138 | CP-I | Pyra | — | Imi | — |
| R-139 | CP-I | Pyra | — | TMX | — |
| R-140 | CP-I | Azoxy | — | Fip | — |
| R-141 | CP-I | Azoxy | — | Clo | — |
| R-142 | CP-I | Azoxy | — | Imi | — |
| R-143 | CP-I | Azoxy | — | TMX | — |
| R-144 | CP-I | Trifl | — | Fip | — |
| R-145 | CP-I | Trifl | — | Clo | — |
| R-146 | CP-I | Trifl | — | Imi | — |
| R-147 | CP-I | Trifl | — | TMX | — |
| R-148 | CP-I | KM | — | Fip | — |
| R-149 | CP-I | KM | — | Clo | — |
| R-150 | CP-I | KM | — | Imi | — |
| R-151 | CP-I | KM | — | TMX | — |
| R-152 | CP-I | Fluo | — | Fip | — |
| R-153 | CP-I | Fluo | — | Clo | — |
| R-154 | CP-I | Fluo | — | Imi | — |
| R-155 | CP-I | Fluo | — | TMX | — |
| R-156 | CP-I | Fluoxa | — | Fip | — |
| R-157 | CP-I | Fluoxa | — | Clo | — |
| R-158 | CP-I | Fluoxa | — | Imi | — |
| R-159 | CP-I | Fluoxa | — | TMX | — |

TABLE 2-continued

| No | I | II (1) | II (1) | III (1) | IV (2) |
|---|---|---|---|---|---|
| R-160 | CP-I | Pen | — | Fip | — |
| R-161 | CP-I | Pen | — | Clo | — |
| R-162 | CP-I | Pen | — | Imi | — |
| R-163 | CP-I | Pen | — | TMX | — |
| R-164 | CP-I | Penthi | — | Fip | — |
| R-165 | CP-I | Penthi | — | Clo | — |
| R-166 | CP-I | Penthi | — | Imi | — |
| R-167 | CP-I | Penthi | — | TMX | — |
| R-168 | CP-I | Seda | — | Fip | — |
| R-169 | CP-I | Seda | — | Clo | — |
| R-170 | CP-I | Seda | — | Imi | — |
| R-171 | CP-I | Seda | — | TMX | — |
| R-172 | CP-I | Pyra | — | Clo | Fip |
| R-173 | CP-I | Pyra | — | Imi | Fip |
| R-174 | CP-I | Pyra | — | TMX | Fip |
| R-175 | CP-I | Azoxy | — | Clo | Fip |
| R-176 | CP-I | Azoxy | — | Imi | Fip |
| R-177 | CP-I | Azoxy | — | TMX | Fip |
| R-178 | CP-I | Trifl | — | Fip | Fip |
| R-179 | CP-I | Trifl | — | Clo | Fip |
| R-180 | CP-I | Trifl | — | Imi | Fip |
| R-181 | CP-I | Trifl | — | TMX | Fip |
| R-182 | CP-I | KM | — | Clo | Fip |
| R-183 | CP-I | KM | — | Imi | Fip |
| R-184 | CP-I | KM | — | TMX | Fip |
| R-185 | CP-I | Fluo | — | Clo | Fip |
| R-186 | CP-I | Fluo | — | Imi | Fip |
| R-187 | CP-I | Fluo | — | TMX | Fip |
| R-188 | CP-I | Fluoxa | — | Clo | Fip |
| R-189 | CP-I | Fluoxa | — | Imi | Fip |
| R-190 | CP-I | Fluoxa | — | TMX | Fip |
| R-191 | CP-I | Pen | — | Clo | Fip |
| R-192 | CP-I | Pen | — | Imi | Fip |
| R-193 | CP-I | Pen | — | TMX | Fip |
| R-194 | CP-I | Penthi | — | Clo | Fip |
| R-195 | CP-I | Penthi | — | Imi | Fip |
| R-196 | CP-I | Penthi | — | TMX | Fip |
| R-197 | CP-I | Seda | — | Clo | Fip |
| R-198 | CP-I | Seda | — | Imi | Fip |
| R-199 | CP-I | Seda | — | TMX | Fip |
| R-200 | CP-I | Pyra | — | Clo | Fip |
| R-201 | CP-I | Pyra | — | Imi | Fip |
| R-202 | CP-I | Pyra | — | TMX | Fip |
| R-203 | CP-I | Pyra | Fluo | Fip | — |
| R-204 | CP-I | Pyra | Fluoxa | Fip | — |
| R-205 | CP-I | Pyra | Pen | Fip | — |
| R-206 | CP-I | Pyra | Seda | Fip | — |
| R-207 | CP-I | Pyra | Fluo | Imi | — |
| R-208 | CP-I | Pyra | Fluoxa | Imi | — |
| R-209 | CP-I | Pyra | Pen | Imi | — |
| R-210 | CP-I | Pyra | Seda | Imi | — |
| R-211 | CP-I | Pyra | Fluo | TMX | — |
| R-212 | CP-I | Pyra | Fluoxa | TMX | — |
| R-213 | CP-I | Pyra | Pen | TMX | — |
| R-214 | CP-I | Pyra | Seda | TMX | — |
| R-215 | CP-I | Pyra | Fluo | Clo | — |
| R-216 | CP-I | Pyra | Fluoxa | Clo | — |
| R-217 | CP-I | Pyra | Pen | Clo | — |
| R-218 | CP-I | Pyra | Seda | Clo | — |
| R-219 | CP-I | Pyra | Fluo | Imi | Fip |
| R-220 | CP-I | Pyra | Fluoxa | Imi | Fip |
| R-221 | CP-I | Pyra | Pen | Imi | Fip |
| R-222 | CP-I | Pyra | Seda | Imi | Fip |
| R-223 | CP-I | Pyra | Fluo | TMX | Fip |
| R-224 | CP-I | Pyra | Fluoxa | TMX | Fip |
| R-225 | CP-I | Pyra | Pen | TMX | Fip |
| R-226 | CP-I | Pyra | Seda | TMX | Fip |
| R-227 | CP-I | Pyra | Fluo | Clo | Fip |
| R-228 | CP-I | Pyra | Fluoxa | Clo | Fip |
| R-229 | CP-I | Pyra | Pen | Clo | Fip |
| R-230 | CP-I | Pyra | Seda | Clo | Fip |
| R-231 | CP-I | Azoxy | Fluo | Fip | — |
| R-232 | CP-I | Azoxy | Fluoxa | Fip | — |
| R-233 | CP-I | Azoxy | Pen | Fip | — |
| R-234 | CP-I | Azoxy | Seda | Fip | — |
| R-235 | CP-I | Azoxy | Fluo | Imi | — |
| R-236 | CP-I | Azoxy | Fluoxa | Imi | — |
| R-237 | CP-I | Azoxy | Pen | Imi | — |
| R-238 | CP-I | Azoxy | Seda | Imi | — |
| R-239 | CP-I | Azoxy | Fluo | TMX | — |
| R-240 | CP-I | Azoxy | Fluoxa | TMX | — |
| R-241 | CP-I | Azoxy | Pen | TMX | — |
| R-242 | CP-I | Azoxy | Seda | TMX | — |
| R-243 | CP-I | Azoxy | Fluo | Clo | — |
| R-244 | CP-I | Azoxy | Fluoxa | Clo | — |
| R-245 | CP-I | Azoxy | Pen | Clo | — |
| R-246 | CP-I | Azoxy | Seda | Clo | — |
| R-247 | CP-I | Azoxy | Fluo | Imi | Fip |
| R-248 | CP-I | Azoxy | Fluoxa | Imi | Fip |
| R-249 | CP-I | Azoxy | Pen | Imi | Fip |
| R-250 | CP-I | Azoxy | Seda | Imi | Fip |
| R-251 | CP-I | Azoxy | Fluo | TMX | Fip |
| R-252 | CP-I | Azoxy | Fluoxa | TMX | Fip |
| R-253 | CP-I | Azoxy | Pen | TMX | Fip |
| R-254 | CP-I | Azoxy | Seda | TMX | Fip |
| R-255 | CP-I | Azoxy | Fluo | Clo | Fip |
| R-256 | CP-I | Azoxy | Fluoxa | Clo | Fip |
| R-257 | CP-I | Azoxy | Pen | Clo | Fip |
| R-258 | CP-I | Azoxy | Seda | Clo | Fip |
| R-259 | CP-I | Trifl | Fluo | Fip | — |
| R-260 | CP-I | Trifl | Fluoxa | Fip | — |
| R-261 | CP-I | Trifl | Pen | Fip | — |
| R-262 | CP-I | Trifl | Seda | Fip | — |
| R-263 | CP-I | Trifl | Fluo | Imi | — |
| R-264 | CP-I | Trifl | Fluoxa | Imi | — |
| R-265 | CP-I | Trifl | Pen | Imi | — |
| R-266 | CP-I | Trifl | Seda | Imi | — |
| R-267 | CP-I | Trifl | Fluo | TMX | — |
| R-268 | CP-I | Trifl | Fluoxa | TMX | — |
| R-269 | CP-I | Trifl | Pen | TMX | — |
| R-270 | CP-I | Trifl | Seda | TMX | — |
| R-271 | CP-I | Trifl | Fluo | Clo | — |
| R-272 | CP-I | Trifl | Fluoxa | Clo | — |
| R-273 | CP-I | Trifl | Pen | Clo | — |
| R-274 | CP-I | Trifl | Seda | Clo | — |
| R-275 | CP-I | Trifl | Fluo | Imi | Fip |
| R-276 | CP-I | Trifl | Fluoxa | Imi | Fip |
| R-277 | CP-I | Trifl | Pen | Imi | Fip |
| R-278 | CP-I | Trifl | Seda | Imi | Fip |
| R-279 | CP-I | Trifl | Fluo | TMX | Fip |
| R-280 | CP-I | Trifl | Fluoxa | TMX | Fip |
| R-281 | CP-I | Trifl | Pen | TMX | Fip |
| R-282 | CP-I | Trifl | Seda | TMX | Fip |
| R-283 | CP-I | Trifl | Fluo | Clo | Fip |
| R-284 | CP-I | Trifl | Fluoxa | Clo | Fip |
| R-285 | CP-I | Trifl | Pen | Clo | Fip |
| R-286 | CP-I | Trifl | Seda | Clo | Fip |
| R-287 | CP-I | KM | Fluo | Fip | — |
| R-288 | CP-I | KM | Fluoxa | Fip | — |
| R-289 | CP-I | KM | Pen | Fip | — |
| R-290 | CP-I | KM | Seda | Fip | — |
| R-291 | CP-I | KM | Fluo | Imi | — |
| R-292 | CP-I | KM | Fluoxa | Imi | — |
| R-293 | CP-I | KM | Pen | Imi | — |
| R-294 | CP-I | KM | Seda | Imi | — |
| R-295 | CP-I | KM | Fluo | TMX | — |
| R-296 | CP-I | KM | Fluoxa | TMX | — |
| R-297 | CP-I | KM | Pen | TMX | — |
| R-298 | CP-I | KM | Seda | TMX | — |
| R-299 | CP-I | KM | Fluo | Clo | — |
| R-300 | CP-I | KM | Fluoxa | Clo | — |
| R-301 | CP-I | KM | Pen | Clo | — |
| R-302 | CP-I | KM | Seda | Clo | — |
| R-303 | CP-I | KM | Fluo | Imi | Fip |
| R-304 | CP-I | KM | Fluoxa | Imi | Fip |
| R-305 | CP-I | KM | Pen | Imi | Fip |
| R-306 | CP-I | KM | Seda | Imi | Fip |
| R-307 | CP-I | KM | Fluo | TMX | Fip |
| R-308 | CP-I | KM | Fluoxa | TMX | Fip |
| R-309 | CP-I | KM | Pen | TMX | Fip |
| R-310 | CP-I | KM | Seda | TMX | Fip |
| R-311 | CP-I | KM | Fluo | Clo | Fip |
| R-312 | CP-I | KM | Fluoxa | Clo | Fip |
| R-313 | CP-I | KM | Pen | Clo | Fip |
| R-314 | CP-I | KM | Seda | Clo | Fip |

With respect to their intended use as a seed treatment, the following ternary mixtures of compound I and two fungicidal compounds IIA set forth below in table 1 are preferred.

With respect to their intended use as a seed treatment, the following ternary mixtures of compound I and two fungicidal compounds IIA set forth below in table 1 are preferred.

Each of the above-mentioned inventive mixtures can further comprise one or more insecticides, fungicides, herbicides.

For use according to the present invention, the mixtures according to the invention can be converted into the customary formulations, for example solutions, emulsions, suspensions, dusts, powders, pastes and granules. The use form depends on the particular intended purpose; in each case, it should ensure a fine and even distribution of the inventive mixtures. The formulations are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical formulations may also comprise auxiliaries which are customary in agrochemical formulations. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i. e. compounds that impart a modified flowability to formulations, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds the respective active compounds present in the inventive mixtures and, if appropriate, further active substances, with at least one solid carrier.

Granules, e. g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Examples for formulation types are:

1. Composition Types for Dilution with Water i) Water-Soluble Concentrates (SL, LS)

10 parts by weight of compounds of the inventive mixtures are dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.

ii) Dispersible Concentrates (DC)

20 parts by weight of compounds of the inventive mixtures are dissolved in 70 parts by weight of cyclohexanone with addition of 10 parts by weight of a dispersant, e. g. polyvinylpyrrolidone. Dilution with water gives a dispersion. The active substance content is 20% by weight.

iii) Emulsifiable Concentrates (EC)

15 parts by weight of compounds of the inventive mixtures are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of compounds of the inventive mixtures are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of compounds of the inventive mixtures are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of compounds of the inventive mixtures are ground finely with addition of 50 parts by weight of dispersants and wetting agents and prepared as water-dispersible or water-soluble granules by means of technical appliances (e. g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of compounds of the inventive mixtures are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of compounds of the inventive mixtures are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of compounds of the inventive mixtures are ground finely and mixed intimately with 95 parts by weight of finely divided kaolin. This gives a dustable composition having an active substance content of 5% by weight.

x) Granules (GR, FG, GG, MG)

0.5 parts by weight of compounds of the inventive mixtures is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of compounds of the inventive mixtures are dissolved in 90 parts by weight of an organic solvent, e. g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The compounds of the inventive mixtures are employed in a purity of from 90% to 100%, preferably from 95% to 100% (according to NMR spectrum).

The compounds of the inventive mixtures can be used as such or in the form of their compositions, e. g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive mixtures.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive mixtures.

The compounds of the inventive mixtures may also be used successfully in the ultralow-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive mixtures in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

As already explained above, the mixture of the invention is not restricted to a physical mixture. Thus the compounds I and II can be applied as a physical mixture or separately. The compounds contained in the mixtures as defined above can be applied simultaneously, that is jointly or separately, or in succession, the sequence, in the case of separate application, generally not having any effect on the result of the control measures.

According to this invention, the compound I and compound II is to be understood to denote, that at least the compound I and compound II occur simultaneously at the site of action (i.e. the pests, such as harmful fungi and animal pests such as insects, arachnids or nematodes to be controlled or their habitats such as infected plants, plant propagation materials, particularly seeds, surfaces, materials or the soil as well as plants, plant propagation materials, particularly seeds, soil, surfaces, materials or rooms to be protected from fungal or animal attack) in a effective amount.

This can be obtained by applying the compound I and compound II simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In the mixtures of the present invention, the weight ratio of the compounds generally depends from the properties of the compounds of the inventive mixtures.

The compounds of the inventive mixtures can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E. g., kits may include the compound I and compound II and/or an adjuvant component and/or a further pesticidal compound (e.g. insecticide or herbicide) and/or a growth regulator component). One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i. e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual compounds of the inventive mixtures formulated as composition (or formulation) such as parts of a kit or parts of the inventive mixture may be mixed by the user himself in a spray tank and further auxiliaries may be added, if appropriate (tank mix).

In a further embodiment, either individual compounds of the inventive mixtures formulated as composition or partially premixed components, e. g. components comprising the compound I and compound II may be mixed by the user in a spray tank and further auxiliaries and additives may be added, if appropriate (tank mix).

In a further embodiment, either individual components of the composition according to the invention or partially premixed components, e. g. components comprising the compound I and compound II, can be applied jointly (e.g. after tankmix) or consecutively.

As said above, the present invention comprises a method for controlling harmful fungi, wherein the harmful fungi, their habitat, breeding grounds, their locus or the plants to be protected against pest attack, the soil or plant propagation material (preferably seed) are treated with an pesticidally effective amount of an inventive mixture.

Advantageously, the inventive mixtures are suitable for controlling the following harmful fungi:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e.g. *B. oryzae* on rice and turfs; *Blumeria* (formerly *Erysiphe*) graminis (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporiodes*); *Corticium* spp., e. g. *C. sasakii* (sheath blight) on rice; *Corynespora cassiicola* (leaf spots) on soybeans and ornamentals;

*Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis* tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyre*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *berella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella angulata* on vines, pome fruits and other plants and *G. gossypii* on cotton; Grain-staining complex on rice; *Guignardia bewellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meiborniae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phornopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phylophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphandermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Odium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reilana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis* corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The inventive mixtures are also suitable for controlling fungal diseases occurring in the protection of materials (e. g. wood, paper, paint dispersions, fiber or fabrics) and in the protection of stored products. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisiae.*

They are particularly important for controlling a multitude of harmful fungi on various cultivated plants, such as bananas, cotton, vegetable species (for example cucumbers, beans and cucurbits), barley, grass, oats, coffee, potatoes, corn, fruit species, rice, rye, soya, tomatoes, grapevines, wheat, ornamental plants, sugar cane and also on a large number of plant propagation materials (preferably seeds).

"Locus" means a plant, plant propagation material (preferably seed), soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

As said above, the present invention comprises a method for improving the health of plants, wherein the plant, the locus where the plant is growing or is expected to grow or plant propagation material, from which the plant grows, is treated with an plant health effective amount of an inventive mixture.

The term "plant health effective amount" denotes an amount of the inventive mixtures, which is sufficient for achieving plant health effects as defined herein. More exemplary information about amounts, ways of application and suitable ratios to be used is given below. Anyway, the skilled artisan is well aware of the fact that such an amount can vary in a broad range and is dependent on various factors, e.g. the treated cultivated plant or material and the climatic conditions.

The term "effective amount" comprises the terms "plant health effective amount" and/or "pesticidally effective amount" as the case may be.

When preparing the mixtures, it is preferred to employ the pure active compounds, to which further active compounds against pests, such as insecticides, herbidices, fungicides or else herbicidal or growth-regulating active compounds or fertilizers can be added as further active components according to need.

The inventive mixtures are employed by treating the fungi or the plants, plant propagation materials (preferably seeds), materials or soil to be protected from fungal attack with a pesticidally effective amount of the active compounds I and II. The application can be carried out both before and after the infection of the materials, plants or plant propagation materials (preferably seeds) by the harmful fungi.

Preferably, the inventive mixtures are employed by treating the fungi or the plants or soil to be protected from pesticidal attack via foliar application with a pesticidally effective amount of the active compounds. Also herein, the application can be carried out both before and after the infection of the plants by the harmful fungi.

In the method of combating harmful fungi depending on the type of compound and the desired effect, the application rates of the mixtures according to the invention are from 0, 1 g/ha to 10000 g/ha, preferably 2 g/ha to 2500 g/ha, more preferably from 5 to 1000 g/ha, most preferably from 10 to 750 g/ha, in particular from 20 to 500 g/ha.

Plants and as well as the propagation material of said plants, which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, mixtures according to the present invention can be applied (as seed treatment, spray treatment, in furrow or by any other means) also to plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phylophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

As mentioned at the outset, in a preferred embodiment of the invention, the inventive mixtures are used for the protection of the seed and the seedlings' roots and shoots, preferably the seeds.

Seed treatment can be made into the seedbox before planting into the field.

For seed treatment purposes, the weight ration in the inventive mixtures generally depends from the properties of the compounds of the inventive mixtures.

Customary formulations, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)

H Gel-Formulations (GF)

I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying the inventive mixture and compositions thereof, respectively, on to plant propagation material, especially seeds, are known in the art, and include but not limited to, seed dressing, seed coating, seed dusting, seed soaking, seed film coating, seed multilayer coating, seed encrusting, seed dripping, and seed pelleting.

In a preferred embodiment, the compounds or the compositions thereof, respectively, are applied on to the plant propagation material by a method such that germination is not induced, e. g. by seed dressing, pelleting, coating and dusting.

In the treatment of plant propagation material (preferably seed), the application rates of the inventive mixture are generally for the formulated product (which usually comprises from 10 to 750 g/l of the active(s)).

The invention also relates to the propagation products of plants, and especially the seed comprising, that is, coated with and/or containing, a mixture as defined above or a composition (customary formulation) comprising the inventive mixture of two or more active ingredients or a mixture of two or more compositions each providing one of the active ingredients. The plant propagation material (preferably seed) comprises the inventive mixtures in an amount of from 0.1 g to 10 kg per 100 kg of plant propagation material (preferably seed), preferably 0.1 g to 1 kg per 100 kg of plant propagation material (preferably seed).

The separate or joint application of the compounds of the inventive mixtures is carried out by spraying or dusting the seeds, the seedlings, the plants or the soils before or after sowing of the plants or before or after emergence of the plants.

In accordance with one variant of soil application, a further subject of the invention is in furrow treatment, which comprises adding a solid or liquid formulation comprising the inventive mixtures to the open furrow, in which seeds have been sown or, alternatively, applying seeds and formulation simultaneously to the open furrow.

The mixture of the invention is also suitable for combating animal pests, preferably invertebrate pests.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

Invertebrate pests controlled by the mixture of the invention include for example: insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocol-letis blancardella, Lobesia botrana, Loxostege sticticalis, Lymantria dispar, Lymantria monacha, Lyonetia clerkella, Malacosoma neustria, Mamestra brassicae, Orgyia pseu-dotsugata, Ostrinia nubilalis, Panolis flammea, Pectinophora gossypiella, Peridroma saucia, Phalera bucephala, Phthorimaea operculella, Phyllocnistis citrella, Pieris bras-sicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus*

*lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;*

Siphonatera, e.g. *Xenopsylla cheopsis, Ceratophyllus* spp.

The mixture of the invention is useful for the control of nematodes, especially plant parasitic nematodes such as root knot nematodes, *Meloidogyne hapla, Meloidogyne incognita, Meloidogyne javanica,* and other *Meloidogyne species;* cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species;

Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the mixture of the invention is used for controlling insects or arachnids, in particular insects of the orders Lepidoptera, Coleoptera, Thysanoptera and Homoptera and arachnids of the order Acarina. The mixture of the invention is particularly useful for controlling insects of the order Thysanoptera and Homoptera.

The mixtures of the present invention show synergistic action against the pests to be controlled. Synergism can be described as an interaction where the combined effect of a mixture of two or more compounds is greater than the sum of the individual effects of each of the compounds. The presence of a synergistic effect, in terms of percent control, between two mixing partners (X and Y) can be calculated using the Colby equation (Colby, S. R., 1967, Calculating Synergistic and Antagonistic Responses in Herbicide Combinations, Weeds, 15, 20-22):

$$E = X + Y - \frac{XY}{100}$$

In Colby's formula X and Y are the % control observed for the individual compounds at a given concentration. E is the expected combined control effect, which would be expected in the absence of synergism, if the compounds were applied together at the same concentrations of solo application. When the control effect observed for the mixture (i.e. the observed combined control effect) is greater than the expected combined control effect (E) as calculated from Colby's formula, then the observed effect is synergistic.

EXAMPLES

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Microtests

The active compounds were formulated separately as a stock solution having a concentration of 10000 ppm in dimethyl sulfoxide.

The compound of formula I was used as a commercial finished formulation and diluted with water to the stated concentration of the active compound.

Example 1 Activity Against the Late Blight Pathogen *Phylophthora Infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 1.

TABLE 1

| Active compound/ active mixture | Concentration [ppm] | Mixture | Observed efficacy [%] | Calculated efficacy according to Colby [%] | Synergism [%] |
|---|---|---|---|---|---|
| Compound I | 4 | — | 6 | — | — |
| Pyraclostrobin | 0.063 | — | 28 | — | — |
| Compound I Pyraclostrobin | 4 0.063 | 63.5:1 | 62 | 32 | 30 |

Example 2 Activity Against Leaf Blotch on Wheat Caused by *Septoria Tritici* (Septtr)

The stock solutions were mixed according to the ratio, pipetted onto a micro titer plate (MTP) and diluted with water to the stated concentrations. A spore suspension of *Septoria tritici* in an aqueous biomalt solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 2.

TABLE 2

| Active compound/ active mixture | Concentration [ppm] | Mixture | Observed efficacy [%] | Calculated efficacy according to Colby [%] | Synergism [%] |
|---|---|---|---|---|---|
| Compound I | 63 | — | 0 | — | — |
|  | 4 | — | 0 | — | — |
| Fluxapyroxad | 0.063 | — | 54 | — | — |
| Pyraclostrobin | 0.004 | — | 63 | — | — |
| Compound I Fluxapyroxad | 63 0.063 | 1000:1 | 85 | 54 | 31 |
| Compound I Pyraclostrobin | 0.25 0.004 | 60:1 | 69 | 43 | 26 |

Example 3 Activity Against *Alternaria Solani* (Alteso)

The stock solutions were mixed according to the ratio, pipetted onto a micro titer plate (MTP) and diluted with water to the stated concentrations. A spore suspension of *Alternaria solani* in an aqueous biomalt solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 3.

TABLE 3

| Active compound/ active mixture | Concentration [ppm] | Mixture | Observed efficacy [%] | Calculated efficacy according to Colby [%] | Synergism [%] |
|---|---|---|---|---|---|
| Compound I | 1 | — | 0 | — | — |
| Pyraclostrobin | 0.001 | — | 16 | — | — |
| Compound I Pyraclostrobin | 1 0.001 | 1000:1 | 39 | 16 | 23 |

The test results show that by virtue of strong synergism, the activity of the mixtures according to the invention is considerably higher than had been predicted using Colby's formula.

We claim:
1. A mixture comprising,
1) an insecticidal compound of formula I

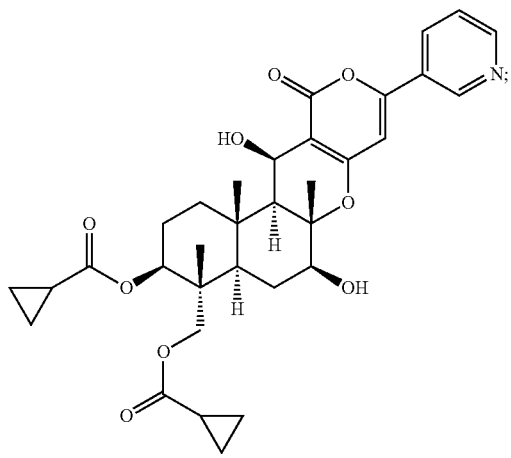

(I)

and fluxapyroxadin synergistic effective amounts, wherein the weight ratio of compound I: fluxapyroxad is 1:1 to 1500:1.

2. A method for improving the health of plants and/or increasing the yield, wherein the plant, the locus where the plant is growing or is expected to grow or plant propagation material from which the plant grows is treated with an effective amount of the mixture of claim 1.

3. A method for controlling pests, wherein the pests, their habitat, food supply, breeding grounds, their locus or the plants to be protected against pest attack, the soil or plant propagation material are treated with an effective amount of the mixture of claim 1.

4. A method for protection of plant propagation materials and/or of plants growing therefrom from pests comprising contacting the plant propagation materials with the mixture of claim 1 in pesticidally effective amounts.

5. A pesticidal composition, comprising a liquid or solid carrier and a mixture as defined in claim 1.

6. A method for improving the health of plants and/or increasing the yield, wherein the plant, the locus where the plant is growing or is expected to grow or plant propagation material from which the plant grows is treated with an effective amount of the composition of claim 5.

7. A method for protection of plant propagation materials and/or of plants growing therefrom from pests comprising contacting the plant propagation materials with the composition of claim 5 in pesticidally effective amounts.

8. A method for controlling pests, wherein the pests, their habitat, food supply, breeding grounds, their locus or the plants to be protected against pest attack, the soil or plant propagation material are treated with an effective amount of the composition of claim 5.

* * * * *